(12) United States Patent
Workman et al.

(10) Patent No.: US 9,693,730 B2
(45) Date of Patent: Jul. 4, 2017

(54) WIRELESS INFANT HEALTH MONITOR

(71) Applicant: OWLET PROTECTION ENTERPRISES LLC, Provo, UT (US)

(72) Inventors: Kurt Gibbons Workman, Provo, UT (US); Tanor G. Hodges, Centerville, UT (US); Jacob B. Colvin, Alpine, UT (US); Wyatt M. Felt, Provo, UT (US); Jordan J. Monroe, Provo, UT (US); Zachary David Bomsta, Provo, UT (US)

(73) Assignee: Owlet Protection Enterprises LLC, Provo, UT (US)

( * ) Notice: Subject to any disclaimer, the term of this patent is extended or adjusted under 35 U.S.C. 154(b) by 0 days.

(21) Appl. No.: 14/001,503

(22) PCT Filed: Aug. 23, 2013

(86) PCT No.: PCT/US2013/056511
§ 371 (c)(1),
(2) Date: Aug. 24, 2013

(87) PCT Pub. No.: WO2014/035836
PCT Pub. Date: Mar. 6, 2014

(65) Prior Publication Data
US 2015/0157263 A1    Jun. 11, 2015

Related U.S. Application Data

(60) Provisional application No. 61/798,642, filed on Mar. 15, 2013, provisional application No. 61/693,267, (Continued)

(51) Int. Cl.
*A61B 5/1455* (2006.01)
*A61B 5/00* (2006.01)
(Continued)

(52) U.S. Cl.
CPC .......... *A61B 5/6807* (2013.01); *A61B 5/0013* (2013.01); *A61B 5/0205* (2013.01);
(Continued)

(58) Field of Classification Search
CPC . A61B 5/0002; A61B 5/1455; A61B 5/14551; A61B 5/14552; A61B 5/14532; A61B 5/0059
(Continued)

(56) References Cited

U.S. PATENT DOCUMENTS 5,505,199 A    4/1996   Kim
5,515,865 A    5/1996   Scanlon
(Continued)

FOREIGN PATENT DOCUMENTS

CA        2334964       3/2009
CN       101108125      1/2008
(Continued)

OTHER PUBLICATIONS

International Search Report and Written Opinion for PCT/US2013/056511 mailed Mar. 12, 2015.
(Continued)

*Primary Examiner* — Eric Winakur
*Assistant Examiner* — Chu Chuan (JJ) Liu
(74) *Attorney, Agent, or Firm* — Workman Nydegger

(57) ABSTRACT

A system for wirelessly monitoring the health of an infant comprising a sensing module removably disposed within a wearable article. At least a portion of the sensing module can be in contact with an infant's foot. The sensing module can include a processing unit configured to receive and process health readings received by the sensing module. A wireless transmitter can also be in communication with the processing unit. The wireless transmitter can be configured to transmit the processed health readings to a receiving station.
(Continued)

The receiving station can indicate an alarm if the processed health readings indicate a health trend that falls outside of a particular threshold.

21 Claims, 8 Drawing Sheets

Related U.S. Application Data filed on Aug. 25, 2012, provisional application No. 61/722,795, filed on Nov. 6, 2012.

(51) Int. Cl.
*A61B 5/0205* (2006.01)
*A61B 5/11* (2006.01)
*A61B 5/0245* (2006.01)
*G08B 21/02* (2006.01)

(52) U.S. Cl.
CPC .............. *A61B 5/0245* (2013.01); *A61B 5/11* (2013.01); *A61B 5/14551* (2013.01); *A61B 5/14552* (2013.01); *A61B 5/6829* (2013.01); *A61B 5/6898* (2013.01); *A61B 5/7221* (2013.01); *A61B 5/7275* (2013.01); *A61B 5/742* (2013.01); *A61B 5/747* (2013.01); *G08B 21/0211* (2013.01); *A61B 5/0002* (2013.01); *A61B 5/746* (2013.01); *A61B 2503/04* (2013.01); *G08B 21/0208* (2013.01)

(58) Field of Classification Search
USPC ....... 600/300, 301, 309, 310, 316, 322, 323, 600/326, 338, 340, 344, 473, 476; 356/41

See application file for complete search history.

(56) References Cited

U.S. PATENT DOCUMENTS

| | | | | |
|---|---|---|---|---|
| 5,830,137 | A * | 11/1998 | Scharf | 600/323 |
| 5,842,982 | A * | 12/1998 | Mannheimer | 600/340 |
| 6,047,201 | A | 4/2000 | Jackson | |
| 6,208,897 | B1 | 3/2001 | Jorgenson | |
| 6,289,238 | B1 | 9/2001 | Besson | |
| 6,492,634 | B2 | 12/2002 | Marchitto | |
| 6,498,652 | B1 * | 12/2002 | Varshneya | A61B 5/113 356/477 |
| 6,553,242 | B1 | 4/2003 | Sarussi | |
| 6,553,256 | B1 | 4/2003 | Jorgenson | |
| 6,879,850 | B2 * | 4/2005 | Kimball | A61B 5/14551 600/336 |
| 7,006,855 | B1 | 2/2006 | Sarussi | |
| 7,035,432 | B2 * | 4/2006 | Szuba | A61B 5/1128 382/103 |
| 7,171,251 | B2 | 1/2007 | Sarussi et al. | |
| 7,215,991 | B2 | 5/2007 | Besson | |
| 7,359,741 | B2 | 4/2008 | Sarussi | |
| 7,590,438 | B2 | 9/2009 | Sarussi et al. | |
| 7,603,152 | B2 | 10/2009 | Sarussi et al. | |
| 7,606,607 | B2 | 10/2009 | Sarussi et al. | |
| 7,613,490 | B2 | 11/2009 | Sarussi et al. | |
| 7,650,176 | B2 | 1/2010 | Sarussi et al. | |
| 2002/0013538 | A1 * | 1/2002 | Teller | A61B 5/0002 600/549 |
| 2002/0133067 | A1 * | 9/2002 | Jackson, III | A61B 5/02416 600/323 |
| 2003/0229276 | A1 | 12/2003 | Sarussi | |
| 2004/0034293 | A1 | 2/2004 | Kimball | |
| 2004/0249299 | A1 * | 12/2004 | Cobb | A61B 5/0205 600/529 |
| 2005/0113655 | A1 | 5/2005 | Hull | |
| 2007/0073119 | A1 | 3/2007 | Wobermin | |
| 2009/0112769 | A1 | 4/2009 | Dicks | |
| 2009/0216556 | A1 * | 8/2009 | Martin et al. | 705/3 |
| 2009/0247849 | A1 * | 10/2009 | McCutcheon et al. | 600/323 |
| 2010/0081901 | A1 | 4/2010 | Buice et al. | |
| 2011/0288379 | A1 | 11/2011 | Wu | |
| 2012/0157757 | A1 | 6/2012 | Ten Eyck | |
| 2012/0179479 | A1 | 7/2012 | Waterson | |
| 2012/0245447 | A1 * | 9/2012 | Karan et al. | 600/309 |
| 2013/0261415 | A1 * | 10/2013 | Ashe | A61B 5/14552 600/324 |

FOREIGN PATENT DOCUMENTS

| | | |
|---|---|---|
| EP | 1139865 | 10/2001 |
| IL | 121079 | 1/2005 |
| JP | 2008194323 | 8/2008 |
| WO | 2012025829 | 3/2012 |
| WO | 2012082297 | 6/2012 |

OTHER PUBLICATIONS

International Search Report and Written Opinion for PCT/US2013/056511 Mailed Dec. 10, 2013.

Supplementary European Search Report, EP 13832064 dated May 3, 2016.

* cited by examiner

WIRELESS INFANT HEALTH MONITOR

CROSS-REFERENCE TO RELATED APPLICATIONS

The present application is a 35 U.S.C. §371 U.S. National of PCT Patent Application No. PCT/US13/56511 filed Aug. 23, 2013, entitled "Wireless Infant Health Monitor," which claims the benefit of U.S. Provisional Application Ser. No. 61/798,642 entitled "Wireless Infant Health Monitor", filed on Mar. 15, 2013, U.S. Provisional Application Ser. No. 61/693,267 entitled "SmartOx", filed on Aug. 25, 2012, and U.S. Provisional Application Ser. No. 61/722,795 entitled "Owlet Baby Monitor", filed on Nov. 6, 2012. The entire content of each of the aforementioned applications is incorporated by reference herein in its entirety.

BACKGROUND OF THE INVENTION

1. The Field of the Invention

The present invention relates generally to infant monitoring equipment.

2. Background and Relevant Art

Every year thousands of babies die from Sudden Infant Death Syndrome ("SIDS"). Because the specific causes of SIDS may be difficult to determine, many parents exert tremendous effort and worry checking on the health of their baby. To aid parents in this effort, various products for monitoring a baby's health, particularly while the baby is sleeping, exist.

For example, many parents use an intercom system that allows them to listen to their baby. In particular, a parent may be alerted to an issue if a long period time of passes without them hearing any noise over the intercom. One will understand, however, that this may not provide a parent with enough notice to intervene before a health issue becomes serious or fatal to the baby.

Accordingly, there are a number of problems in the art that can be addressed.

BRIEF SUMMARY OF THE INVENTION

Implementations of the present invention overcome one or more of the foregoing or other problems in the art with systems, methods, and apparatus that wirelessly monitor the health of a baby. In particular, at least one implementation of the present invention monitors a child's blood oxygen level and indicates an alert when an abnormal trend is identified.

Implementations of the present invention include a system for wirelessly monitoring the health of an infant. The system can comprise a sensing module removably disposed within a wearable article. At least a portion of the sensing module can be in contact with an infant's foot. The sensing module can include a processing unit configured to receive and process health readings received by the sensing module. A wireless transmitter can also be in communication with the processing unit. The wireless transmitter can be configured to transmit the processed health readings to a receiving station. The receiving station can indicate an alarm if the processed health readings indicate a health trend that falls outside of a particular threshold.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof, which are illustrated, in the appended drawings. It should be noted that the figures are not drawn to scale, and that elements of similar structure or function are generally represented by like reference numerals for illustrative purposes throughout the figures. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Implementations of the present invention extend to systems, methods, and apparatus that wirelessly monitor the health of a baby. In particular, at least one implementation of the present invention monitors a child's blood oxygen level and indicates an alert when an abnormal trend is identified.

Figure 1:
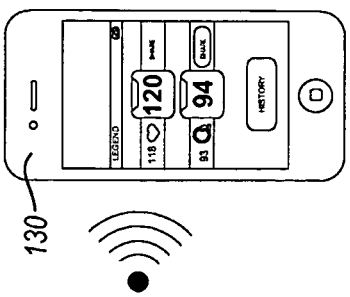
FIG. 1 illustrates a schematic diagram of a system for monitoring the health of an infant in accordance with an implementation of the present invention.
Figure 1:
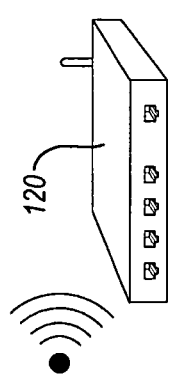
Figure 1:
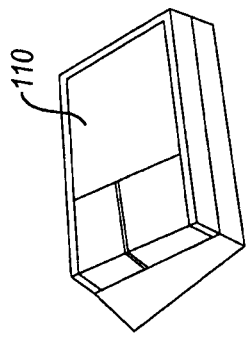
Figure 1:
Figure 1:
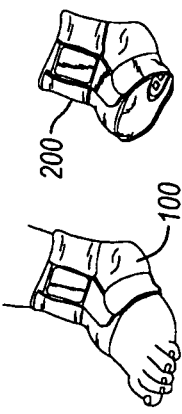

For example, FIG. 1 illustrates a schematic diagram of a system for monitoring the health of an infant in accordance with an implementation of the present invention. In particular, FIG. 1 depicts a sensing module disposed within a sock (shown by element 100) that is in communication with a receiving station 110. The receiving station 110 is in turn can be in communication with an internet gateway 120 (e.g., a cable modem, a router, a DSL modem, an Ethernet port, etc.). The internet gateway 120 is shown communicating with a computerized device in this implementation a smart phone 130. The smart phone 130 can display data that was originally gathered by the sensing unit (shown in element 100).

Figure 3A:
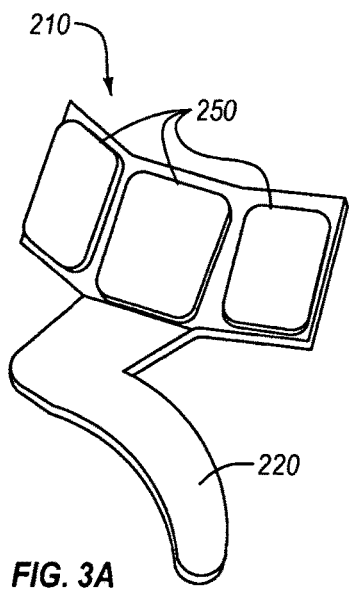
FIG. 3A illustrates a sensor module in accordance with an implementation of the present invention.
Figure 3B:
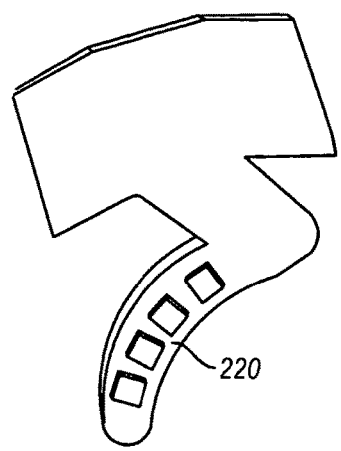
FIG. 3B illustrates another view of the sensor module of FIG. 3A.
Figure 4:
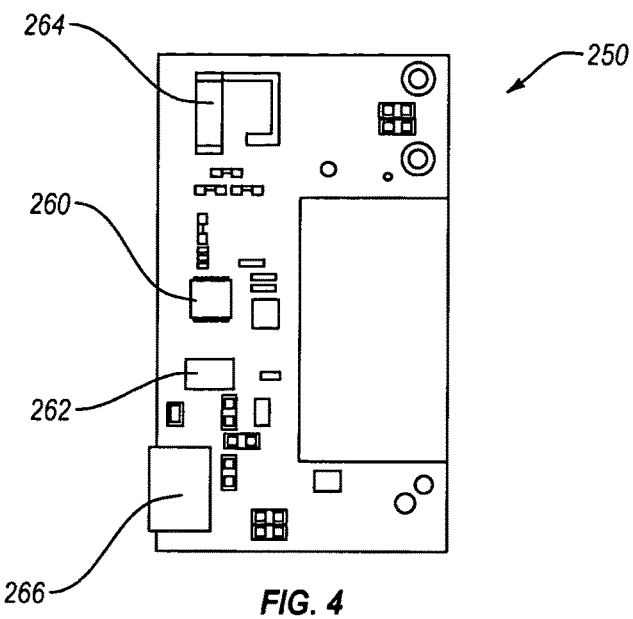
FIG. 4 depicts an implementation of a sensing module circuit board of the present invention.

In at least one implementation, the sensing module 210 comprises a pulse oximeter 220 (shown in FIG. 3B) in communication with a processing unit 250 (shown in FIG. 4). The pulse oximeter 220 can be positioned such that a sensing portion of the pulse oximeter 220 is in sufficient contact with an infant's foot as to receive a pulse oximetry reading. The pulse oximeter 220 can then provide raw data pulse oximetry data to the processing unit 250.

FIG. 1 depicts the sensing module disposed within a wearable article, in particular, a sock 200. In at least one implementation, the sock 200 consists of a "foot-wrap" or "sock" that wraps around the infant's foot and/or ankle. The sock 200 can include the necessary electronics to generate a pulse oximeter reading, for example from the infant's foot/ankle. The raw electrical signals can then be processed by the processing unit 250 on the sock to generate a heart rate value and an SpO2 or Oxygen value as well as other related data.

Once the processing unit 250 receives the raw pulse oximetry data, in at least one implementation, the processing unit 250 processes the raw data. In particular, the processing unit 250 can reformat the data from a raw form to a compressed form. The processing unit 250 can then provide the compressed data to the wireless transmitter 260 (shown in FIG. 4) that is also located within the sock.

The wireless transmitter 260 and the processing unit 250 can be located on a common circuit board. In some cases, processing the data at the processing unit before transmitting the data with the wireless transmitter 260 can result in significant battery savings, as compared to transmitting the raw data. Additionally, processing the data with the processing unit 250 before transmitting the data can improve the data integrity and lower the error rate associated with the data.

Once the data has been processed and transmitted, a receiving station 110 can receive and further analyze the data. In particular, the receiving station 110 can process the data to identify negative health trends within the pulse oximetry data. For example, the receiving station 110 can identify that the reported oxygen level of the infant is below a particular threshold. Additionally, in at least one implementation, the receiving station 110 can also identify if the sensing module 210 is running low on battery, if the transmitted signal strength is low, or other functions that relate to the operation of the present invention.

If the receiving station 110 detects a potential negative trend in the pulse oximetry data or if the receiving station 110 detects a problem within the system (e.g., low battery, poor signal strength, etc.) the receiving station 110 can provide an indication of the problem. For example, in at least one implementation, the receiving station 110 can sound an alarm, display a notification on a visual indicator located on the receiving station 110, or otherwise send a message.

Further, in at least one implementation, the receiving station 110 can display the interpretations of the various data that it is receiving. For example, the receiving station 110 can show a graph tracking the oxygen level of an infant over time. Similarly, the receiving station 110 can display information relating to the heart rate of the infant. Additionally, the receiving station 110 can display historical information relating to the received data. For example, the receiving station 110 can display an average oxygen level for the past hour. In general, the receiving station 110 can utilize the received information to display a variety of useful data that would fall within the present invention.

In at least one implementation, after the receiving station 110 has received and further analyze the data, the receiving station 110 can transmit the data to an internet gateway 120, such as a wireless router. For example, the receiving station 110 can transmit to an internet gateway 120 over a Wi-Fi bridge. Once the data has been received by the internet gateway 120, the data can be transmitted over the internet to a remote computing device 130 or web portal. In at least one implementation, the remote computing device 130 can be located within the same local network as the internet gateway 120 such that the data is only transmitted locally and is not transmitted over the internet. Similarly, in at least one implementation, the wireless transmitter 260 and the processing unit 250 can transmit information directly to the remote computing device 130 (e.g., a smart phone).

In particular, in at least one implementation, the data can be transmitted to a smart phone 130. In the case that a negative trend is identified, the smart phone can sound an alert. Additionally, in at least one implementation, the remote computing device 130 can access a historical record of health recordings. For example, a parent of an infant can access a historical record of the infant's oxygen level and provide the record to the infant's doctor. The accessed historical record can be stored by the remote computing device, the receiving station, or some other web based storage cache.

Similarly, the internet gateway 120 can transmit the data to a web portal. For example, the data can be transmitted to an associated webpage that is password protected. A user of the present invention can then access the data through the associated webpage.

One will understand, that the embodiments described above are only exemplary and that a system of the present invention can comprise a fewer number or a greater number of components. For example, in at least one implementation, the present invention may only include the sock 200 and sensing module 210 and the receiving station 110. In this implementation, the receiving station 110 could alert a user to any information of interest, including negative health trends.

Similarly, in another implementation, the present invention can comprise only the sock 200 and sensing module 210 and an internet gateway 120. In this implementation, the sock 200 and sensing module 210 can communicate to the internet gateway 120 through a wireless protocol. The internet gateway 120 can then transmit information to a remote computing device 130 of interest.

Additionally, in at least one implementation, the present invention can comprise only the sock 200 and sensing module 210. For example, in this implementation, the sensing module 210 can comprise an alarm, such that when a negative health trend is detected, the sensing module 210 alerts a parent. Further, as mentioned above, the present invention can comprise only the sock 200 and sensing module 210 and a remote computing device 130.

FIG. 2 illustrates a wearable article (e.g., a sock 200) and sensing module 210 that is configured to be disposed within the wearable article. In particular, FIG. 2 depicts an implementation of the present invention that comprises a sock 200 that is adapted to contain the sensing module 210. In at least one implementation, the sock 200 can comprise a unique double-layer strapping mechanism and stretchable material that wraps around the infant's foot, creating a tight wrap, which will keep ambient light from interfering with signals generated by LEDs contained within the pulse oximeter sensor 220. For example, in at least one implementation, the pulse oximeter sensor 220 is under the outer strap 230 and against the skin.

In at least one implementation, the sock 200 is configured for the sensing module 210 to be removed from the sock 200. For example, FIGS. 2C and 2D shows the sensing module 200 disposed within a pocket 240 within the sock 200. One will understand that the ability to remove the sensing module 210 from the sock 200 provides several benefits. For example, a sock 200 can easily be laundered by simply removing the sensing module 210 and washing the sock. Additionally, the same sensing module 210 can be used in socks 200 of different size, by simply removing the sensing module 210 from a sock 200 of a first size and inserting it into a sock 200 of a second size.

Additionally, in at least one implementation the sensing module 210 can be housed in a water-resistant material. In particular, the housing can be comprised of silicone or plastic. The housing may include a re-sealable opening for access to an external cable for charging and serial communication. In another implementation, the electronics can be charged via an induction charging set-up.

Figure 2A:
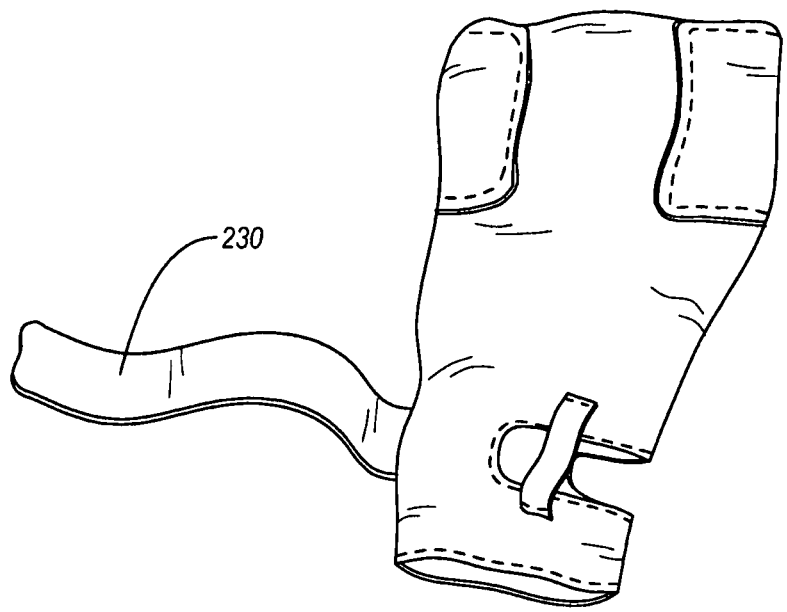
FIG. 2A illustrates a wearable article in accordance with an implementation of the present invention.
Figure 2B:
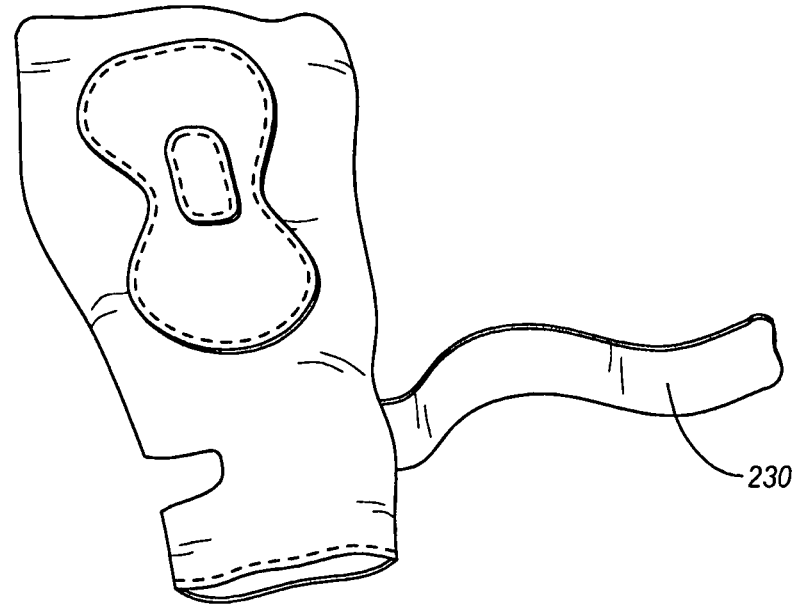
FIG. 2B illustrates another view of the wearable article of FIG. 2A.
Figure 2C:
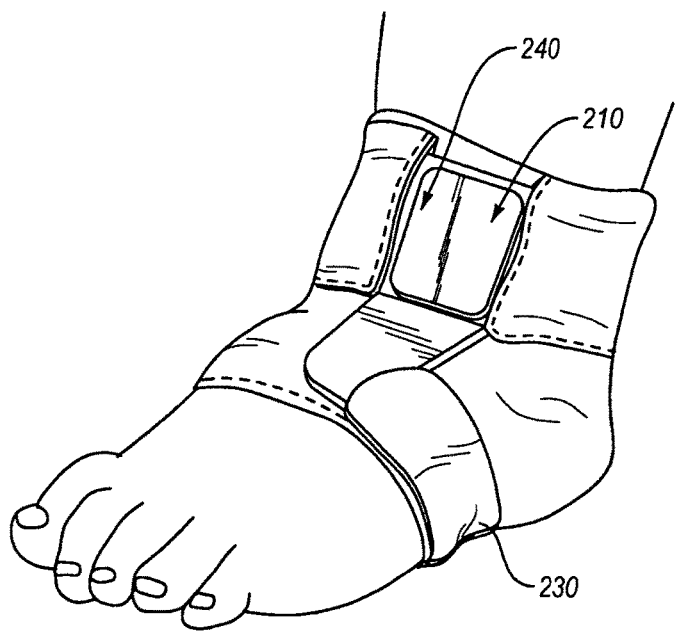
FIG. 2C illustrates the wearable article of FIG. 2A disposed on an infant's foot.
Figure 2D:
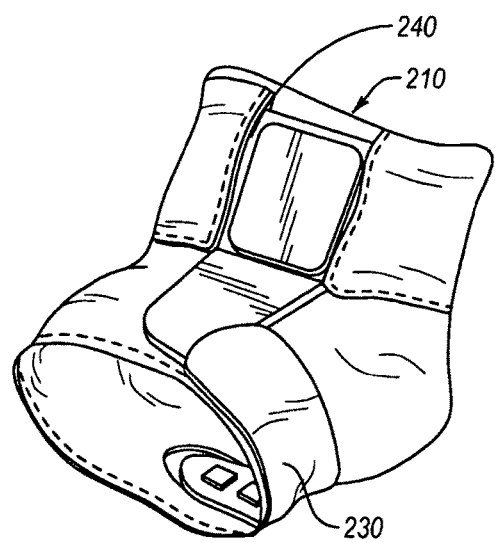
FIG. 2D illustrates yet another view of the wearable article of FIG. 2A.

FIGS. 2C and 2D illustrates an implementation of the wearable article from FIGS. 2A and 2B being disposed upon an infant's foot. In particular, FIG. 2C depicts the sensing module 210 disposed within the sock 200 such that the sensing module 210 is primarily located around the ankle of an infant. Placing the sensing module 210 around the ankle of the infant may have the benefits of providing greater security to the sensing module 210. For example, placing the sensing module 210 around the infant's ankle may make it more difficult for the infant to kick the sensing module 210 off. Additionally, placing the sensing module 210 around the infant's ankle may also provide more room for the sensing module 210 than if the module was placed around the child's foot. However, one will understand that in at least one implementation, the sensing module 210 can be placed such that the module is not on the infant's ankle.

As depicted in FIG. 2C, the upper part of the sock can secure around the infant's ankle. The lower part of the sock can secure around the infants foot. In at least one implementation, the straps on the sock can be secured by Velcro. Properly applying the straps of the present invention can create a strapping system that minimizes the infant's ability to kick the sock off.

In at least one implementation, the sock can also comprise a pouch 240 configured to receive the sensing module 210. The pouch 240 can comprise a zipper that allows the pouch to securely open and close. Additionally, in at least one implementation, the pouch can comprise buttons, Velcro, snaps, or any other apparatus or useful combination of apparatuses to close the pouch.

The sensing module 210, which is receivable into the pouch 240, can comprise an outer layer of Velcro or other alignment feature. In particular, the Velcro or alignment feature can be attached to the pulse oximeter sensor 220 (shown in FIGS. 3A and 3B). This may allow the pulse oximeter sensor 220 to be securely fastened to outer strap 230, such that the pulse oximeter sensor 220 is secure and in close contact with the skin of the infant's foot.

Additionally, in at least one implementation, the pulse oximeter sensor 220 can be encased within a silicone-housed strap that contains the emitting and receiving electronics of the pulse oximetry system. These sensors can include a combination of LED lights and photoreceptors. In some cases, multiple sensors can allow the pulse oximeter sensor 220 to continue to obtain strong pulse oximetry signals despite changes in foot size.

Figure 3C:
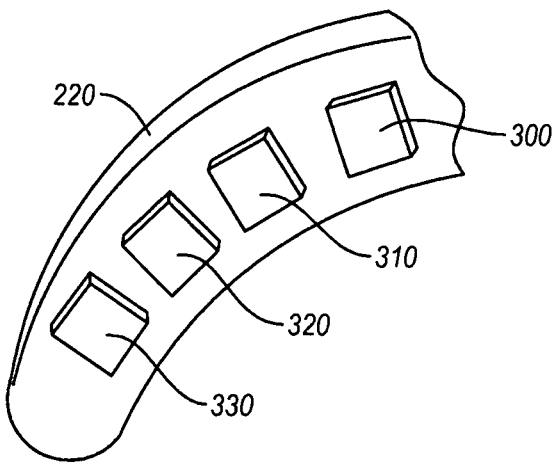
FIG. 3C illustrate an implementation of a pulse oximeter of the present invention.
Figure 3D:
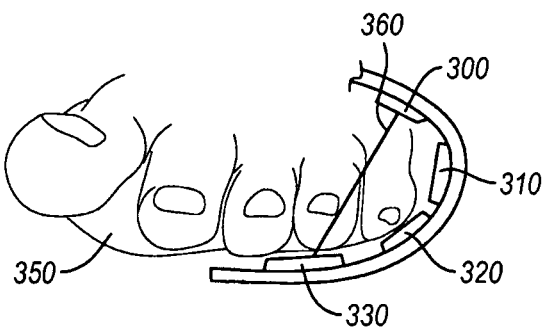
FIG. 3D illustrate another implementation of a pulse oximeter of the present invention.
Figure 3E:
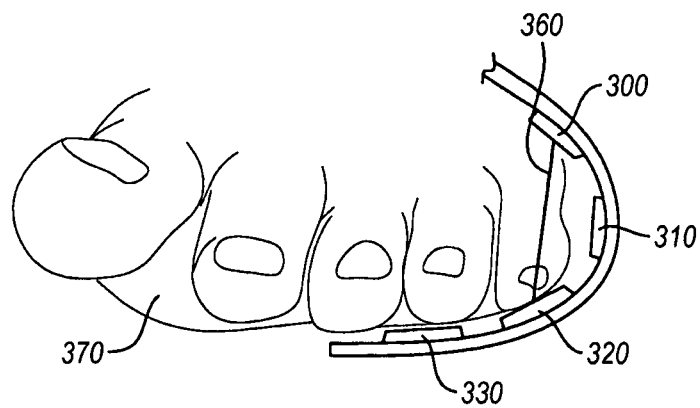
FIG. 3E illustrates yet another implementation of a pulse oximeter of the present invention.

For example, a processing unit within the sensing module 210 may execute an algorithm that finds the best possible combination of LED emitters and photoreceptors, which allows for the best possible pulse oximetry readings. Additionally, the sensing module 210 can execute an algorithm that optimizes the power usage of the LED emitters and photoreceptors. For example, FIGS. 3C-3E depict a multi-sensor mechanism for optimum spO2 and pulse readings.

In some situations, the optimal location and combination of LED emitters and photoreceptors can change for example, as a baby's foot grows the location of the sensor on the baby's foot can change. To help improve the quality of a sensor reading, in addition to using various combinations of LED emitters and photoreceptors, the sock 200 can also include design features in the strap that allow it to flex and move relative to the electronics housing so that a user can place the strap at the optimum placing on the foot for the reading to occur.

The pulse oximeter sensor 220 that wraps around the infants foot may be comprised of a flexible PC board with attached LED lights and photoreceptors (300, 310, 320, 330). This flexible PC board can be housed in a silicone or other flexible polymer. This housing can include a transparent portion and an opaque portion. Additionally, the pulse oximeter sensor 220 can also include a thermometer to monitor skin temperature, which can affect pulse oximetry readings. The thermometer can also be used to monitor and detect additional health trends within an infant.

As mentioned above, the pulse oximeter sensor 220 can comprise a variety of different LED and photoreceptor combinations (300, 310, 320, 330). As a non-limiting example, the pulse oximeter sensor 220 can comprise one photoreceptor or photodiode and one set of LED's (each at a unique optical frequency), or one photoreceptor or photodiode and two sets of LED's, two photoreceptors or photodiodes and one sets of LED's, or some other combination of multiple LED's and photoreceptors.

For example, FIG. 3C illustrates a depiction of an implementation of a pulse oximeter sensor 220. In pulse oximetry, generally, two lights sources having different wavelengths are passed through an individual. A photoreceptor measures the transmitted wavelengths using known methods and determines a blood oxygen level and a pulse. The depicted sensor 220 comprises a plurality of sensor units 300, 310, 320, 330. In at least one implementation, sensor units 300 and 310 can comprises photoreceptors and sensor units 320 and 330 can comprises LEDs. Specifically, sensor units 320 and 330 can comprise LED units capable of transmitting light at two different wavelengths, for example, red and infrared.

FIG. 3D illustrates a depiction of a cross section of a small foot 350 enclosed within the pulse oximeter sensor 220. As depicted, sensor units 300, 310, 320, and 330 are in contact with the surface of the foot at different points around the circumference of the foot. In at least one implementation of the present invention, the sensing module 210 can determine a combination of sensing units 300, 310, 320, 330 that provides a readable signal at an efficient power level. For example, in FIG. 3C sensing unit 300 and sensing unit 330 may have the strongest communication path 360 with each other and thus may generate the strongest signal.

In contrast, FIG. 3E illustrates a depiction of a cross section of a larger foot 370. In this case, because the foot is larger, the sensing units 300, 310, 320, 330 do not have the same alignment as in FIG. 3C. In particular, sensing unit 300 and sensing unit 320 may have the strongest communication path 360, such that the sensing module 210 uses these units 300, 320 for gathering pulse oximetry data.

Additionally, in at least one implementation, the active LED can be varied to prevent too much heat from developing near the skin of an infant. In particular, it may be possible for an LED to get hot enough that long exposure to the LED causes discomfort or even injury. Thus, in at least one implementation, the active LED can be varied such that no single LED is on long enough to generate excessive heat.

While the above described implementations, relied upon two photoreceptors 300, 310 and two LED units 320, 330 the present invention can also be practiced with a variety of different sensor unit configurations. For example, in at least one implementation, more than four sensor units can be utilized to provide even greater granularity in sensor unit selection. Further, in at least one implementation, there can be more photoreceptors than LED units, or in contrast, more LED units than photoreceptors. Additionally, in at least one implementation, the sensing module 210 can determine that the strongest communication path 360 is not necessarily between LEDs that are opposing each other. In particular, in at least one implementation, the sensing module 210 can determine that adjacent LEDs form the strongest communication path 360.

Additionally, in at least one implementation, multiple photoreceptors can be used to read from a single LED, or in contrast, a single photoreceptor can be used to read from multiple active LEDs. For example, the sensing module 210 can determine that activating three LEDs and receiving at two photoreceptors provides the necessary communication strength for a good reading, while using power most efficiently. Similarly, the sensing module 210 can determine that using a single photoreceptor reading from two LEDs provides the best reading for the lowest amount of power usage. Accordingly, in at least one implementation, the sensing module 210 can determine the ideal LED and photoreceptor configuration by starting at a low (or lowest) power configuration (e.g., one photoreceptor reading one LED) and progressing to a high (or highest) power configuration (e.g., all photoreceptors reading all LEDs) to determine what configuration provides sufficient signal strength for the least amount of power. In at least one implementation, efficient power usage is defined to mean using a configuration of LEDs that consumes the least amount of power while still providing a readable signal. Additionally, in at least one implementation, a readable signal is defined to mean a signal that the processing unit is able to interpret into health data.

In addition, the above-described implementations are not limited to being practiced by the sensing module 210. For example, in at least one implementation, the receiving station or a remote computing device can determine the strongest pathway 360 between two sensor units.

The ability to selectively identify the strongest communication pathway 360 between sensor units can improve the reliability of pulse oximetry data. In particular, if the pulse oximetry sensor 220 moves after being put on an infant's foot, a different strongest communication pathway 360 can be identified to maintain the data quality. Additionally, in at least one implementation, the ability to selectively identify a strongest communication pathway 360 can permit the pulse oximetry sensor 200 to be used on a wide range of foot sizes.

FIG. 4 depicts an implementation of a portion of a processing unit 250. In particular, FIG. 4 depicts a processing unit 250 portion of a sensing module 210. The processing unit 250 can comprise means for processing pulse oximetry data on-site. Specifically, the processing unit can includes all necessary means for processing and filtering the raw pulse oximeter data and relaying that data to a receiving station or other types of wireless transceivers. For example, the processing unit can convert the raw data into a format that can be broadcast over a particular wireless connection (e.g., Bluetooth, RF 915, etc.). One will understand, however, that various transmission formats are known in the art and any number and combination of known transmission formats can be used and remain within the scope of the present invention.

Additionally, the processing unit 250 can receive a raw data signal from the pulse oximeter sensor 210 and filter out both the AC and DC component of the electrical signals sent from the photoreceptor. In at least one implementation, the processing unit can also filter out unwanted noise from movement and external sources. As the processing unit processes and filters the received raw data the processing unit can determine at least a blood oxygen level and a pulse.

In addition to the processing unit 250, in at least one implementation, the sensing module 210 can include at least one power source, such as a battery, that can power the sensing module 210. The battery can be removable and/or rechargeable. In at least one implementation, the sensing module 210 can also include a visual indicator that indicates when the battery is low on power and need replacing.

The sensing module 210 can also include at least one accelerometer 262 that can detect movement that could possibly disrupt the pulse oximeter readings. For example, the normal movements of an infant may negatively impact the readings that are received by the pulse oximeter sensor. Detecting the movement can enable the processing unit 250 to compensate for the movement, or in some cases, recognize a potential false alarm. This can allow for tagging unusual readings that are caused by movement to distinguish them from unusual readings due to abnormal heart rates and other factors. For example, an infant's movements might shake the sensing module 210 loose causing the sensing module to report no pulse and low oxygen levels. However, instead of issuing an alarm, the accelerometer 262 can detect movement and notify the sensing module 210 that the no pulse and low oxygen levels are likely a false alarm.

Additionally, the accelerometer 262 can be used to determine a sleeping position of the infant. It is believed that infants are most at risk for SIDs when they sleep with their face down. Accordingly, the accelerometer 262 may be used to determine whether the infant's foot, and in turn body, is facing upwards or downwards. In determining the infant's position the sensing module 210 may allow readings from the accelerometer 262 to settle and persist for a particular amount of time to avoid false alarms. In at least one implementation, the infant's position can be used in determining when to sound an alarm and what alarm to sound. For example, an alarm may sound if an infant remains face down for a particular period of time. Similarly, the position of the infant may be used to determine whether to elevate an alarm, or to determine whether to signal a false alarm or an emergency alarm.

Additionally, a vibrator or alarm 264 can be disposed within the sensing module 210. The alarm or vibrator 264 can be used to alert a parent when a negative health trend is detected. Also, the vibrator or alarm 264 can be used to stimulate breathing within the baby when a negative trend is detected. In at least one implementation, the vibrator or alarm 264 on the sensing module 210 only activates if an alarm on the receiving station 110 is not available.

The sensing module 210 can also include at least one physical communications port 266. The at least one communications port 266 can be used for recharging the battery within the sensing module, communicating data to the sensing module, updating software within the sensing module, or some other known function. Additionally, in at least one implementation, the sensing module 210 can physically connect to the receiving station for recharging and communication purposes.

In at least one implementation, the sensing module 210 within the sock 200 can be activated by the receiving station 110 by means of "wake-on radio". Alternatively, the sensing module 210 can be activated by detecting the levels of light being received by the photo-diodes to turn on the LED's when the sock is properly oriented on an infant's foot.

Figure 5:
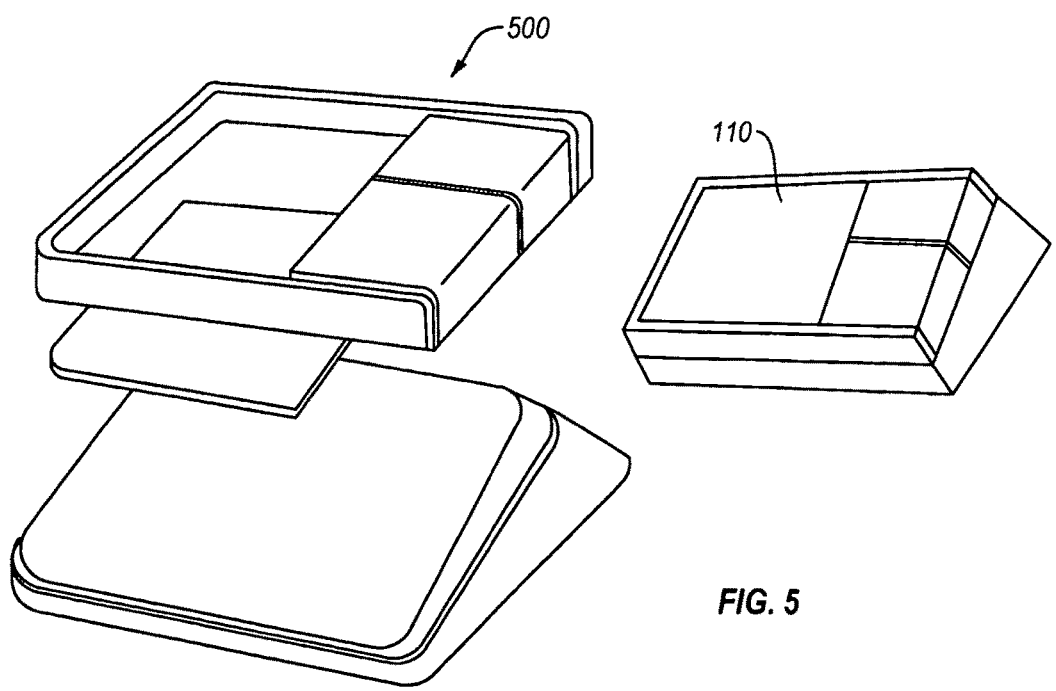
FIG. 5 illustrates an implementation of a receiving station and an implementation of an accompanying receiving station cover.

FIG. 5 illustrates an implementation of a receiving station 110 and an implementation of an accompanying receiving station cover 500. FIG. 5 depicts a receiving station 110 comprising a plastic enclosure with an angled display for aesthetic appeal and functionality. The enclosure can be designed to fit comfortably on a nightstand or counter. An angled display may make it easy to see such that with a quick glance a parent can see the oxygen and heart rate values and/or other important notifications.

Figure 6:
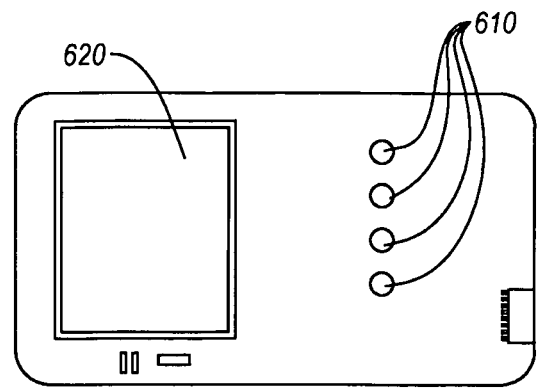
FIG. 6 depicts a circuit board and display associated with an implementation of a receiving station.

FIG. 6 depicts another figure of an implementation of a receiving station 110. The buttons 610 on the enclosure of the receiving station may be of the type shown in the drawing and the picture. The receiving station 110 can receive the wireless transmission signal from a sensing module 210, or from multiple sensing modules 210 disposed within multiple socks attached to different infants. The receiving station 110 can then display the data on an LCD display 620, including information to distinguish between the potentially multiple sensing modules 210.

In at least one implementation, a user can configure the receiving station's 110 response to a particular alarm or to alarms in general. For example, a user can silence a current alert being indicated by the receiving station 110. Similarly, in at least one implementation, a user can configure the receiving station 110 to only indicate an alarm if certain conditions are met. Further, a user can configure the receiving station 110 to only communicate with certain means (e.g., audible alarm, vibration, visual indicator, etc.) and/or to only communicate through certain channels (e.g., only to remote devices, only to local devices, etc.).

Additionally, in at least one implementation, the receiving station 110 can relay the data through a Wi-Fi/wireless bridge to the home or other wireless routers, which then relay the data to a server or to another device on the network. The receiving station 110 can also comprise various LED lights for added clarity to the caregiver. In addition, an ambient light sensor may also signal the receiving station 110 to automatically dim its screen while in a dark room.

The receiving station 110 can also include a means of locally storing the health data for later analysis, upload, and/or product verification. Further, in at least one implementation, the receiving station 110 can also connect to other sensors such as a microphone, video camera, thermometer, or movement sensor/pad. Additionally, the receiving station 110 can comprise the necessary transmission components to communicate with the sensing module 210 (e.g., an RF 915 MHz receiver, Bluetooth) and the internet gateway (e.g., via a Wi-Fi bridge).

In addition, the receiving station 110 can comprise software configured to manage the data received from the sensing module 210. In particular, the software can provide instructions to alert parents if there is possible danger to their child. Since false alarms cause anxiety and unnecessary fear, however, in at least one implementation, the software can include a delayed alarm system. Many infants naturally hold their breath for short periods of time, causing the blood oxygen concentration to drop. Since this can be a normal occurrence, the receiving station 110 software cannot only evaluate the current oxygen level but also any upward and downward trends of the oxygen and heart rate values.

For example, in at least one implementation, the software can identify an abnormal downward trend in the health data, and based on the trend sound an alarm. In contrast, in at least one implementation, the software can identify a normal downward trend in the health data and delay the alarm for a threshold time to determine if the health data will return to normal levels. One will understand that identifying trends within the health data can help limit false alarms due to natural events.

Figure 7:
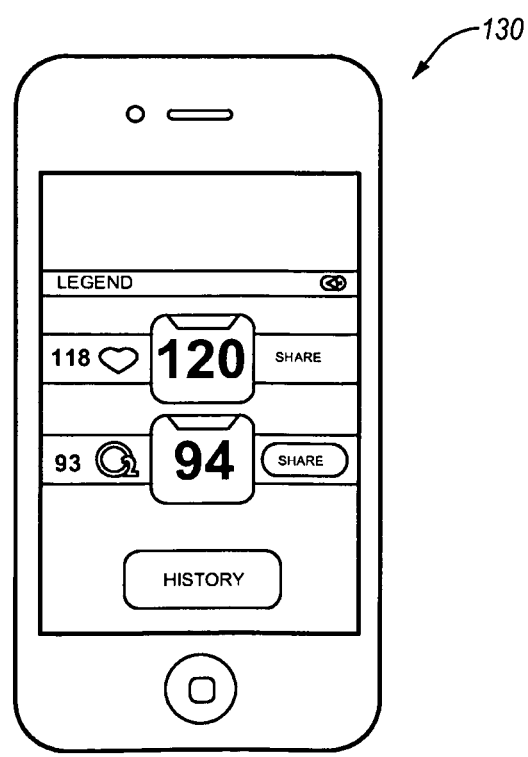
FIG. 7 depicts a smart phone displaying an interface that is associated with the present invention.

FIG. 7 depicts a smart phone 130 displaying an interface that is associated with the present invention. In particular, at least one implementation of the present invention, can communicate with the smart phone 130. Specifically, health data can be communicated with the smart phone 130 through an internet web page or through an application dedicated to communication with the present invention.

In at least one implementation, the webpage or the dedicated application can receive data from the internet gateway 120. The data can be received either through a connection to the internet or through a direct connection over the internal network. The webpage or dedicated software can display, record, and save the oxygen and heart rate values.

This feature can allow the parent/caregiver to see the values in real-time but also to be proactive in the parent's approach to health care. For example, the saved data can allow a caregiver to notice trends in oxygen levels that could prove a useful method for detecting health issues, such as sleep apnea and asthma. These trends can be identified in the form of graphs or history charts that display historical health data. Additionally, the data can also be a means for determining the amount and quality of sleep that the baby is getting. In particular, the software may comprise a share feature that can enable a parent to easily share the health data with another, such as a doctor.

Additionally, upon receiving an alert generated by the receiving station 110, or upon receiving health data that demonstrates a negative trend, the smart phone 130 can also indicate an alert. For example, the smart phone 130 can sound an audible alarm, vibrate, or generate a visual alert. One will appreciate, that there are a multitude of methods for smart phones 130 to alert a user, many of which can be used within the present invention.

Figure 8:
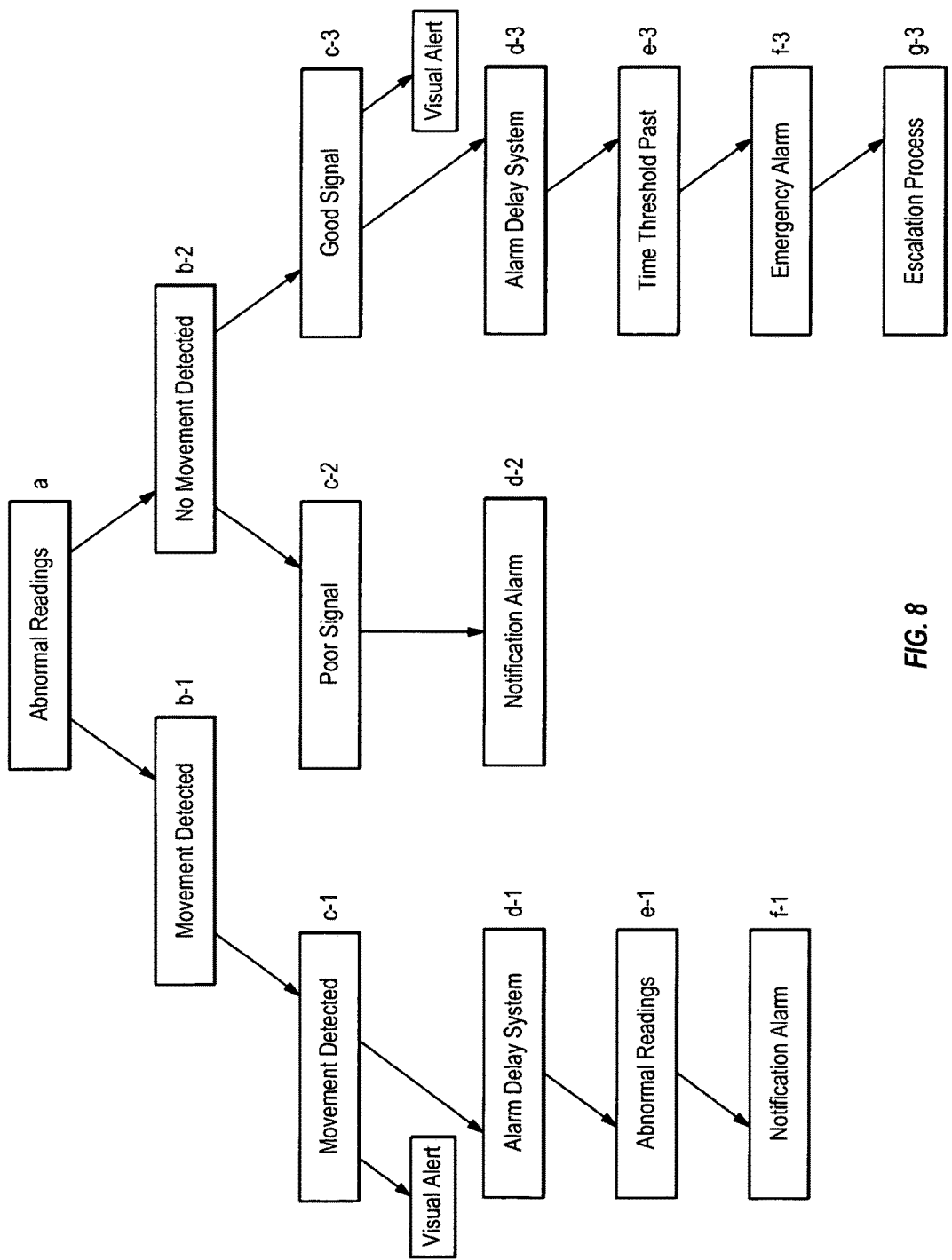
FIG. 8 depicts a logical tree associated with an implementations of the present invention.

FIG. 8 depicts a logical flow chart associated with implementations of the present invention. In particular, FIG. 8 depicts a logical tree chart that describes an implementation of the logic that can be applied to an abnormal reading of health data by software at the sensing module 210, the receiving station 110, the remote computing device 130, or any other computing device associated with the present invention. In general, an abnormal reading can consist of low oxygen levels or oxygen levels above realistic values such as 100 and above. Additionally, abnormal readings also can represent a heart rate that is too high or too low. Further, abnormal readings can also consist of an absence of a pulse oximeter reading or a bad pulse waveform. One will understand, however, that these are just potential reasons that an abnormal reading can occur, and are not meant as an exhaustive list of the abnormalities that the present invention can identify and compensate for.

Returning to FIG. 8, in block "a" an abnormal reading is detected. In at least one implementation, upon detecting an abnormal pulse oximetry reading, the software can determine if an accelerometer 262 that is in contact with the infant is detecting motion. If movement is detected (block b-1), the abnormal reading can be moved to a lower priority, because a moving child is less likely to have a dangerously low oxygen level and movement may be a primary cause of abnormal readings. In response to detecting motion, the software can generate a visual indication that an abnormal reading is being received, but that motion is being detected. For example, the software can generate a message on a remote computing device 130, or the software can display a visual indication on the receiving station.

In the case that abnormal readings continue, even if the software detects motion, the software can enter an alarm delay mode (block d-1). In particular, the software can allow for a threshold amount of time for the health readings to return to a normal level. The amount of the threshold can depend upon the detected oxygen level and the upward or downward trend. If after the threshold amount of time passes, the alarm is still producing abnormal readings (block e-1) then the software can raise the priority of the abnormal readings and signal an alarm. For example, the software can send an indication for an audible alarm (block f-1) on the remote computing device or the receiving station. This alarm can be a different alarm than the alarm used for a verified health concern. In particular, this alarm can be used to signify that the infant may need attention, but is not likely in danger of a detected health issue.

Returning now to box "a" in FIG. 8. If the software detects abnormal readings and no movement is detected, the software can determine the strength of the pulse oximeter signal. For example, the software can determine that the signal from the pulse oximeter sensor is weak (block c-2), that the actual pulse oximeter readings are unreadable, or that the pulse oximeter readings are questionable because of outside influences. If the software determines that the signal is weak then the software can indicate that an alarm be sounded (block d-2). In at least one implementation, however, this alarm is different from the alarm that is sounded if a health concern is detected. Specifically, this alarm can be reserved for situation where an infant may need attention, but it is not a health emergency.

In contrast, the software can determine that the signal from the pulse oximeter sensor is a readable signal (block c-3), or in other words, that the waveform and that SpO2 levels are clearly determined and the wireless signal is good. In this case, the software can indicate that a visual alert should be displayed. Similar to the visual alert described above, this alert can be displayed, for example, within a message on a remote computing device or within the display of the receiving station.

Also similar to above, the software can wait a threshold amount of time to determine if the health data returns to normal (block d-3). If the threshold time passes and the health readings do not return to a normal range (block e-3), the software can indicate that an emergency alarm be indicated (block f-3). In at least one implementation, this alarm is the highest priority alarm. Specifically, this alarm may be the loudest alarm and comprise a distinct sound.

In at least one implementation, this alarm may comprise an escalation process (block g-3). In particular, if the software does not detect a response to the alarm, the software can alert third parties, such as emergency responders or other designated individuals or devices. In at least one implementation of the present invention, a user can customize the priority and alarm that is associated with each of the above situation. For example, a user can specify that no alarm or indication be presented when abnormal readings are accompanied with the detection of motion.

Figure 9:
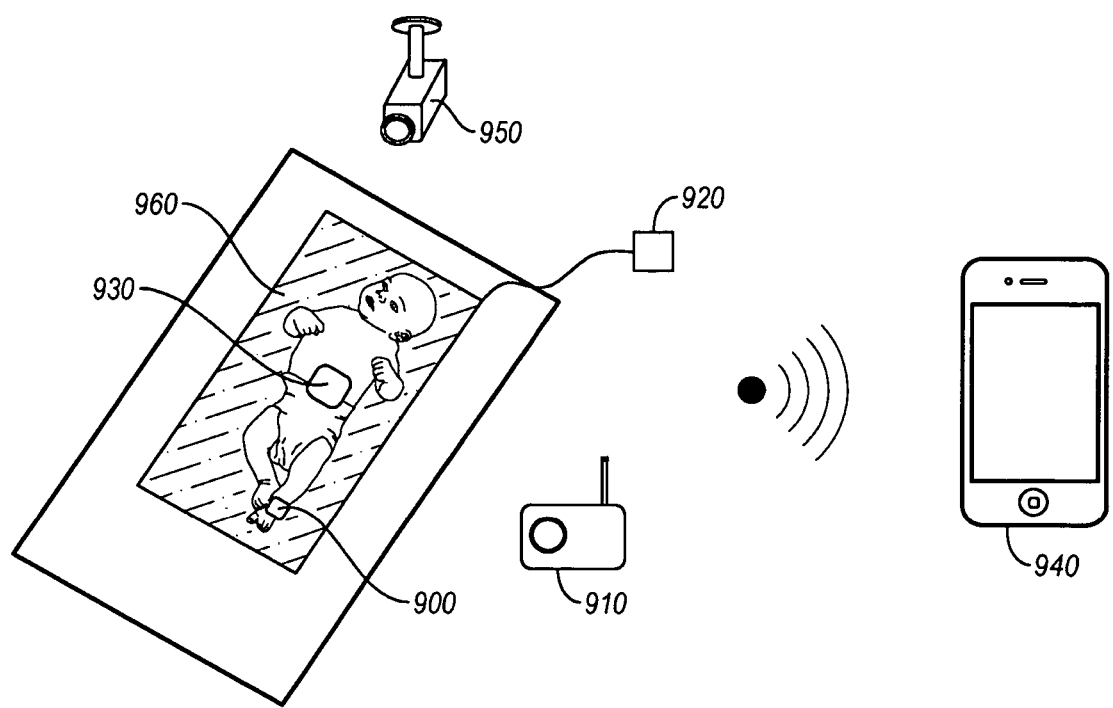
FIG. 9 illustrates a schematic diagram of another implementation of a system for monitoring the health of an infant.

FIG. 9 illustrates a schematic diagram of another implementation of a system for monitoring the health of an infant. In particular, FIG. 9 depicts a sensing module 900 in communication with a variety of other infant monitoring devices for example, an audio monitor 910, a movement sensing pad 960 (including a wireless transmitter 920), a motion detector 930, and a video monitor 950.

In at least one implementation of the present invention, an infant monitoring system can include one or more of these devices in combination. For example, the sensing module 900 may detect an abnormal health reading. In response to the reading, the sensing module can communicate with the video monitor 950 and cause that a video stream or image of the infant be transmitted to a remote computing device 130. In this way, a parent can receive a notification that an abnormal health reading has occurred, while at the same time receiving an image of the infant to help the parent determine whether the notification is an emergency.

Similarly, an implementation of the present invention can incorporate data from the motion sensing pad 960, the motion detector 930, the audio monitor 910, or the video monitor 950 to further investigate abnormal readings. For example, in at least one implementation, in response to receiving an abnormal reading from the sensing module 900, the audio monitor 910 can be utilized to determine if the infant is making any sounds. Similarly, motion detection devices 960, 930, 900 can be used as described above to further identify the appropriate alarm in response to abnormal readings from the sensing module 900.

Accordingly, FIGS. 1-9 provide a number of components, schematics, and mechanisms for wirelessly monitoring the health of an infant. In particular, in at least one implementation, a wireless sensor communicates health data from an infant to a remote computing device. The remote computing device 130 can then be used to monitor the infant's health or to alert an individual to a negative trend in the infant's health. Additionally, in at least one implementation, false alarms can be detected, and in some cases prevented, by analyzing trends in the received health data. One will understand the benefits included within an invention directed towards the above-described system.

The embodiments of the present invention may comprise a special purpose or general-purpose computer including various computer hardware components, as discussed in greater detail below. Embodiments within the scope of the present invention also include computer-readable media for carrying or having computer-executable instructions or data structures stored thereon. Such computer-readable media can be any available media that can be accessed by a general purpose or special purpose computer.

By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A system for wirelessly monitoring the health of an infant, the system comprising:
   a sensing module removably disposed within a wearable article, wherein at least a portion of the sensing module is configured to be in contact with the infant's foot;
   the sensing module comprising:
   a processing unit configured to receive and process health readings received by the sensing module,
   an accelerometer configured to detect movement of the infant's foot,
   the accelerometer also configured to determine a current sleeping position of the infant, wherein when determining the current sleeping position of the infant, readings from the accelerometer are allowed to settle and persist for a particular amount of time, and
   a pulse oximeter configured to detect at least a blood-oxygen level of the infant; and
   wherein the processing unit:
   identifies a particular alarm level based upon a health reading relating to the blood-oxygen level of the infant that was acquired during time periods when the accelerometer did not detect movement of the infant's foot,
   elevates the particular alarm level to a higher alarm level based upon a reading received from the accelerometer that indicates the current sleeping position of the infant is face down, and
   triggers an alarm alert at the higher alarm level.

2. The system as recited in claim 1, wherein the processing unit is configured to:
   activate different combinations of photoreceptors and LEDs from a plurality of photoreceptors and LEDs within the pulse oximeter; and
   identify a particular combination that provides the strongest relative signal.

3. The system as recited in claim 1, further comprising:
   the pulse oximeter comprising a plurality of photoreceptors, wherein the processing unit is configured to activate each of the plurality of photoreceptors independently of each other and identify a particular photoreceptor of the plurality of photoreceptors that receives the strongest relative signal.

4. The system as recited in claim 1, further comprising:
   the pulse oximeter comprising a plurality of LEDs, wherein the processing unit is configured to activate each of the plurality of LEDs independently of each other and identify a particular LED of the plurality of LEDs that generates a strongest relative signal as received by a particular photoreceptor.

5. The system as recited in claim 1, wherein the processing unit is configured to analyze raw pulse oximetry data and compress the data before the data is transmitted to a receiving station.

6. The system as recited in claim 1, wherein a receiving station is configured to indicate an alarm when the processed health readings indicate a health trend that falls outside of a particular threshold.

7. The system as recited in claim 6, wherein the processing unit is configured to disregard abnormal health readings that were detected during the same time period that the accelerometer detected movement.

8. The system as recited in claim 6, further comprising:
   a camera that is in communication with the receiving station, wherein the camera is configured to transmit an image when the processed health readings indicate a health trend that falls outside a particular threshold.

9. The system as recited in claim 8, wherein the camera transmits an image to a mobile phone.

10. The system as recited in claim 6, wherein the receiving station comprises software that processes received health readings from the wireless transmitter.

11. The system as recited in claim in 10, wherein the software is configured to identify false alarm trends in the received health readings.

12. The system as recited in claim 1, further comprising:
    the sensing module comprising a vibrator that is configured to activate in response to abnormal health readings.

13. The system as recited in claim 1, wherein the wearable article comprises a sock.

14. The system as recited in claim 13, wherein the sensing module is removable from a pouch within the wearable article, such that the wearable article is washable.

15. A method, performed at a processing unit in communication with a sensing module, for monitoring the health of an infant, the method comprising:
    receiving data from the sensing module that is configured to be in contact with the infant's foot, wherein the received data comprises:
    motion data received from an accelerometer that is configured to be physically coupled to the infant's foot, wherein the motion data indicates movement by the infant, position data received from the accelerometer, wherein:
    the position data indicates a sleeping position of the infant, and
    the position data from the accelerometer is allowed to settle and persist for a particular amount of time when determining the sleeping position of the infant;
    heart data received from a pulse oximeter, wherein the heart data indicates cardiovascular biometrics associated with the infant;
    determining that a detected health data trend described by the heart data is outside of a threshold;
    elevating an alarm level associated with the detected health data trend to a higher alarm level based upon a reading received from the accelerometer that indicates a current sleeping position of the infant is face down; and triggering an alarm at the higher alarm level.

16. The method as recited in claim 15, wherein determining whether the detected health data trend is outside of the threshold comprises determining that the detected health data trend remains outside of the threshold for a specific amount of time.

17. The method as recited in claim 16, wherein determining that the detected health data trend is outside of the threshold comprises:

receiving information from the accelerometer indicating that the infant is moving; and based upon the detected movement of the infant, tagging the data received from the sensing module.

18. The method as recited in claim 17, wherein upon determining that the reported health data is outside the threshold and that the data received from the sensing module is tagged, determining that the reported health data comprises a false alarm.

19. The method as recited in claim 15, wherein upon determining that the detected health data trend contained within the transmitted data is outside of a threshold, activating a vibrator that is integrated within the sensor module.

20. A system for monitoring the health of an infant, the system comprising:

a sensing module that is configured to be in contact with the infant's foot, wherein the sensing module comprises:

a processing unit configured to receive and process health readings received by the sensing module, an accelerometer configured to detect movement of the infant's foot, the accelerometer also configured to determine a current sleeping position of the infant, wherein when determining the current sleeping position of the infant, readings from the accelerometer are allowed to settle and persist for a particular amount of time, and a pulse oximeter configured to detect at least a blood-oxygen level of the infant; and wherein the processing unit:

identifies a particular alarm level based upon the blood-oxygen level of the infant, elevates the particular alarm level to a higher alarm level based upon a reading received from the accelerometer that indicates the current sleeping position of the infant is face down, and triggers an alarm alert at the higher alarm level.

21. A system for wirelessly monitoring the health of an infant, the system comprising:

a pulse-oximetry sensing module removably disposed within a wearable article, at least a portion of the sensing module is configured to be in contact with the infant's foot;

the pulse-oximetry sensing module comprising:

a processing unit configured to receive and process health readings received by the sensing module, an accelerometer configured to determine a current sleeping position of the infant, wherein when determining the current sleeping position of the infant, readings from the accelerometer are allowed to settle and persist for a particular amount of time, and a pulse oximeter configured to detect at least a blood-oxygen level of the infant; and wherein the processing unit:

generates a particular alarm level based a health reading relating to the blood-oxygen level of the infant, elevates the particular alarm level to a higher alarm level based upon a reading received from the accelerometer that indicates the current sleeping position of the infant is face down, and triggers an alarm alert at the higher alarm level;

a wireless transmitter in communication with the processing unit and a receiving station; and the receiving station comprising a display.

* * * * *